Jan. 19, 1971 D. S. WHISLER Plant Pat. 3,020
ROSE PLANT
Filed Jan. 15, 1969
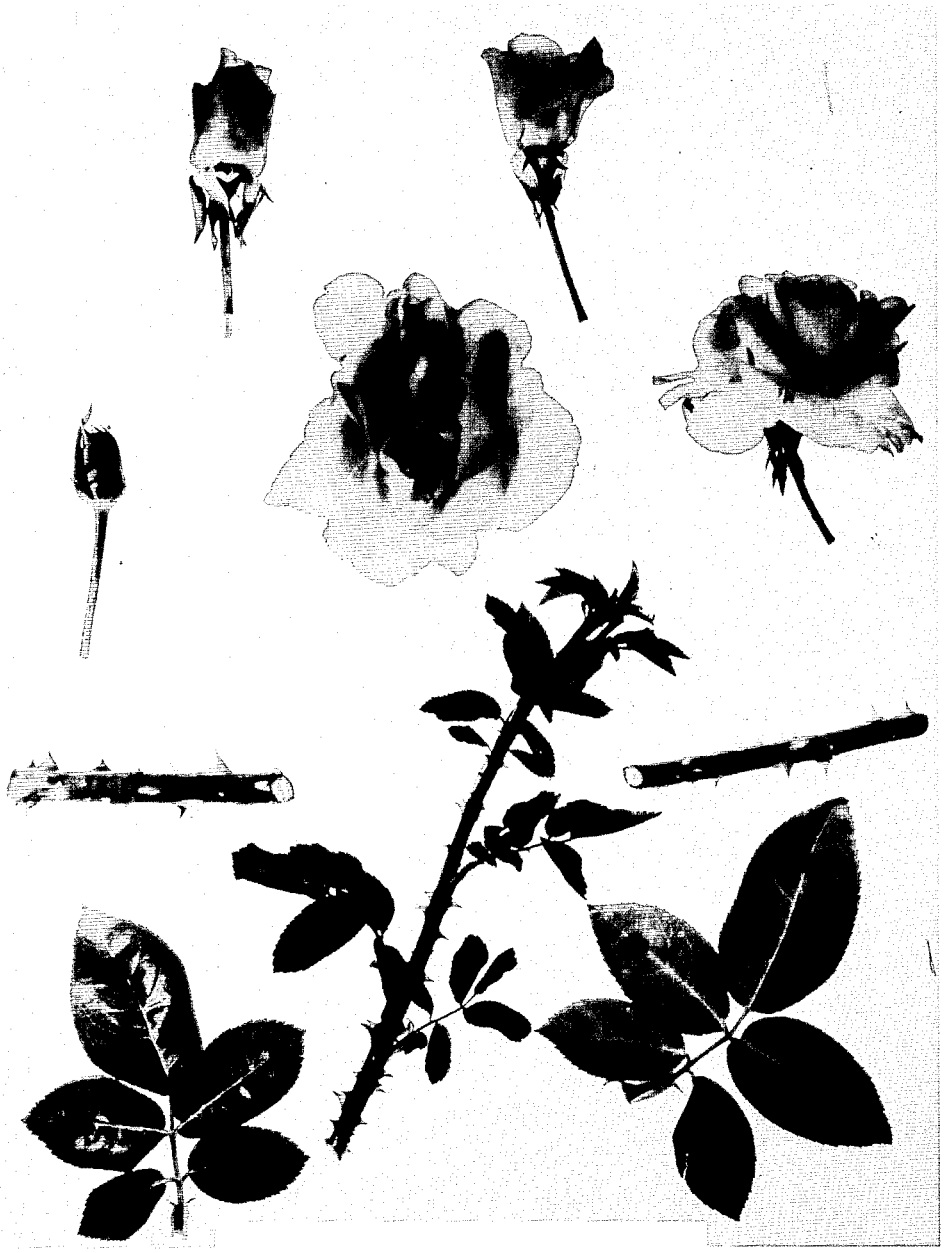
Inventor.
D. S. Whisler
By: Robb & Robb
Attorneys.

United States Patent Office

Plant Pat. 3,020

Patented Jan. 19, 1971

3,020
ROSE PLANT

Dorothy S. Whisler, Shafter, Calif., assignor, by mesne assignments, to Gro-Plant Industries, Inc., Monticello, Fla., a corporation of Florida

Filed Jan. 15, 1969, Ser. No. 791,529
Int. Cl. A01h *5/00*
U.S. Cl. Plt.—20 1 Claim

The present invention relates to a new and distinct variety of rose plant of the hybrid tea class, which was originated by me by crossing the rose variety known as "Rose Queen" (Plant Pat. No. 2,203) with the rose variety known as "Charlotte Armstrong" (Plant Pat. No. 455—expired), the former being the seed parent and the latter being the pollen parent.

As the result of this breeding, I have produced a new and improved rose variety which is distinguished from its parents, as well as from all other rose varieties of which I am aware, as evidenced by the following unique combination of characteristics which are outstanding in the new variety:

(1) A vigorous, basal branching and slightly spreading plant habit;

(2) Moderately glossy foliage, generally in compounds of 7 leaflets, which is dark green when mature, but green-bronze when young, with new growth having a pronounced bronzy-green cast;

(3) Long and strong flowering stems;

(4) A free flowering habit, with the blooms usually borne singly and only occasionally in clusters of 2 blooms per stem;

(5) Straight thorns throughout the plant, often slightly inclined downward but not hooked or recurved, said thorns being reddish bronze when fully mature, and the plant having few prickles anywhere and no hairs;

(6) Attractive, large, ovoid, pointed buds of Signal Red color;

(7) Very bright, high-centered and attractive open blooms of good petalage and Vermillion color, with a stable bloom pigment that finishes Geranium Lake in color without any magenta tones;

(8) Petals of good substance and long life, said petals sometimes being irregularly notched at the apex and dropping cleanly as the bloom finishes;

(9) Large yellow anthers of moderate number, which are held up by red filaments, arranged in a precise whorl around the pistils, said pistils being moderate in number and bunched together in the center of the bloom;

(10) Ovaries which are all enclosed in the receptacle and being only reluctantly fertile, if fertile at all, with sepals which are persistant and recurve; and

(11) A moderate tea flower fragrance.

The principal and significant differences between my new variety and its parents will be apparent from the following comparison:

| Rose Queen (seed parent) | Charlotte Armstrong (pollen parent) | This cultivar |
|---|---|---|
| Orange red—Geranium red under same conditions | Cerise red color | Color development from Orient red, Signal Red, Vermillion, finishing Geranium Lake. |
| 35-40 petals | 25-35 petals | 20-30 petals. |
| Globular bud | Long pointed urn shaped bud. | Long ovoid bud. |
| Opening bloom high-centered | Opening bloom high-centered. | Opening bloom high-centered. |
| Medium red filaments | Yellow and pink filaments. | Dark red filaments. |
| Very fragrant | Moderate fragrance | Moderate fragrance. |
| Stems often short, medium strong, blooms often clustered | Stems long, slender | Stems usually long, moderately heavy. |
| Moderately vigorous | Vigorous | Vigorous. |
| Reddish brown thorns, not hooked but pointing downward, with narrow long base | do | Do. |
| Quite thorny | Moderately thorny | Moderately thorny. |
| Upright habit | Upright spreading from base. | Upright spreading from base. |
| Red prickles on receptacle | Smooth receptacle | Smooth receptacle. |

My new variety somewhat resembles the variety known as "Aztec" (Plant Pat. No. 1,648), but is distinctly different therefrom, even on casual examination, as will be apparent from the following comparison:

| This cultivar | "Aztec" |
|---|---|
| A bright vermillion with yellow complementary pigment | A moderately bright orange with blue complementary pigment. |
| Color stable | Fading bluish. |
| 20-30 petals | 22-28 petals. |
| Moderate tea fragrance | Moderate unusual fragrance. |
| Petal apex often notched | Petal apex smooth. |
| Plant upright and spreading | Plant upright and spreading. |
| Stems usually long and strong | Stems short often nodding. |
| Blooms occasionally in clusters of 2 | Blooms almost always in clusters of of 2 or 3. |
| Leaflets serrate, open pointed | Leaflets dentate, apex often rounded. |
| Thorns bronze brown, straight, may incline slightly down. | Thorns pink brown, slightly hooked downward. |
| New growth bronze red | New growth rosy green. |

Asexual reproduction of my variety by budding, as performed at Shafter, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the British Colour Council, except where general color terms of ordinary dictionary significance are obvious:

Type: Half-hardy; outdoor; seedling; for cut flowers and for garden decoration.
Class: Hybrid tea.
Breeding: Seedling.
*Seed parent.*—"Rose Queen."
*Pollen parent.*—"Charlotte Armstrong."
Propagation: Holds its distinguishing characteristics through succeeding propagations by budding.

FLOWER

Locality where grown and observed: Shafter, Calif.
Flowers borne: Usually singly, but sometimes two to stem; on strong stems of medium length.
Quantity of bloom: Free, outdoors.
Continuity: Continuous.
Fragrance: Moderate.
Bud:
*Peduncle.*—Long; medium caliper; erect; with few red-brown prickles. Color: Reddish bronze.
*Before calyx breaks.*—Size: Medium. Form: Pointed; with foliaceous appendages on the surface of the bud; with slender, entire foliaceous parts extending beyond the tip of the bud equal to ¼ of its length. Color: Scheele's Green, Plate 860/2.

*As calyx breaks.*—Color: Scheele's Green, Plate 860/3.

*As first petal opens.*—Size: Large. Form: Globular. Color: Outside—Signal Red, Plate 719; inside—Orient Red, Plate 819.

*Opening.*—Opens up well.

Bloom:

*Size (when fully open).*—Large; from 5 inches to 6 inches.

*Petalage.*—Double; from 20 to 30 petals; arranged regularly.

*Form.*—High-centered at first, but becoming open-cupped; petals being at first loosely rolled outward, but later becoming loosely flat and rolled outward at maturity.

Petals:

*Appearance.*—Inside: Velvety. Outside: Satiny.

*Shape.*—Outside: Oval; scalloped; with apex having from 1 to 3 or more notches. Intermediate: Ovate; scalloped; with apex having 3 or more notches. Inside: Irregularly scalloped; with apex having 3 or more notches.

This description of a new opened flower was made from a rose grown outdoors during the month of October at Shafter, Calif.:

*Color.*—Outer petal: Outside surface—Orient Red, Plate 819/2; inside surface—Vermillion, Plate 18. Intermediate petal: Outside surface—Signal Red, Plate 719; inside surface—Orient Red, Plate 819. Inner petal: Outside surface—Orient Red, Plate 819/3; inside surface—Vermillion, Plate 18.

This description was made from a rose that was open for three days outdoors during the month of October at Shafter, Calif.:

*Color.*—Outer petal: Outside surface—Signal Red, Plate 719/3; inside surface—Vermillion, Plate 18. Inner petal: Outside surface—Orient Red, Plate 819/3; inside surface—Geranium Lake, Plate 20.

*General color effect.*—Newly opened flower: Vermillion, Plate 18. 3-days open: Vermillion, Plate 18/1.

*Behavior.*—Drop off cleanly.

*Flower longevity.*—On bush in garden: 5 days in September. Cut roses grown outdoors and kept at living-room temperatures: 6 days in September.

REPRODUCTIVE ORGANS

Stamens: Many; arranged regularly about pistils.
*Color.*—Yellow.
Filaments: Medium length; with anthers.
*Color.*—Reddish.
Anthers: Large; open at various times.
*Color.*—Yellow.
Pollen: Moderate abundance.
*Color.*—Yellow.
Pistils: Medium number.
Styles: Uneven; medium length; medium caliper; bunched.
Stigma:
*Color.*—Yellow.
Ovaries: Enclosed in calyx.
Hips: None observed.
Sepals: Permanent; long; recurved.
*Color.*—Brown.
Seeds: None observed.

PLANT

Foliage:

*Leaves.*—Compound of 7 leaflets; normal abundance; medium large; moderately heavy.

*Leaflets.*—Shape: Ovoid; lanceolate. Apex: Mucronate. Base: Round. Margin: Simply serrate.

*Color.*—Mature: Upper surface—dark green; under surface—grey-green. Young: Upper surface—dark green-bronze; under surface—light green-bronze.

*Rachis (the supporting stem of the compound leaf).*—Medium caliper. Upper side: Smooth. Under side: Moderately prickly.

*Stipules.*—Medium length; moderately wide; with medium length points turning out at an angle of 90°; recurved toward the stem.

*Disease resistance.*—Resistant to mildew, as determined by comparison with other varieties grown under comparable conditions at Shafter, Calif.

Growth:

*Habit.*—Upright.

*Growth.*—Vigorous.

*Canes.*—Medium heavy.

*Main stems.*—Color: Green. Thorns: Several; medium length; straight; inclined downward; with long, narrow base. Prickles: Few; color—bronze. Hairs: None.

*Branches.*—Color: Green, but sometimes bronze. Thorns: Several; medium length; straight; with long, narrow base. Prickles: Few; color—brown. Hairs: None.

*New shoots.*—Color: Bronze-red. Thorns: Several; medium length; with long, narrow base. Prickles: Few; color—reddish. Hairs: None.

I claim:

1. A new and distinct variety of rose plant of the hybrid tea class, substantially as herein shown and described, characterized particularly as to novelty by the unique combination of a vigorous, basal branching and slightly spreading plant habit, moderately glossy foliage, generally in compounds of 7 leaflets, which is dark green when mature, but green-bronze when young, with new growth having a pronounced bronze-green cast, long and strong flowering stems, a free flowering habit, with the blooms usually borne singly and only occasionally in clusters of 2 blooms per stem, straight thorns throughout the plant, often slightly inclined downward but not hooked or recurved, said thorns being reddish bronze when fully mature, and the plant having few prickles anywhere and no hairs, attractive, large, ovoid, pointed buds of Signal Red color, very bright, high-centered and attractive open blooms of good petalage and Vermillion color, with a stable bloom pigment that finishes Geranium Lake in color without any magenta tones, petals of good substance and long life, said petals sometimes being irregularly notched at the apex and dropping cleanly as the bloom finishes, large yellow anthers of moderate number, which are held up by red filaments, arranged in a precise whorl around the pistils, said pistils being moderate in number and bunched together in the center of the bloom, ovaries which are all enclosed in the receptacle and being only reluctantly fertile, if fertile at all, with sepals which are persistant and recurve, and a moderate tea flower fragrance.

No references cited.

ROBERT E. BAGWILL, Primary Examiner